United States Patent
Han et al.

(10) Patent No.: US 8,956,643 B2
(45) Date of Patent: Feb. 17, 2015

(54) POROUS BIODEGRADABLE POLYMER SCAFFOLDS FOR IN SITU TISSUE REGENERATION AND METHOD FOR THE PREPARATION THEREOF

(75) Inventors: Dong Keun Han, Seoul (KR); Kwideok Park, Seoul (KR); Jae-Jin Kim, Seoul (KR); Soon Eon Bae, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 955 days.

(21) Appl. No.: 12/473,850

(22) Filed: May 28, 2009

(65) Prior Publication Data

US 2010/0129422 A1  May 27, 2010

(30) Foreign Application Priority Data

Nov. 26, 2008  (KR) .................. 10-2008-0118115

(51) Int. Cl.
| | | |
|---|---|---|
| A61F 2/00 | (2006.01) | |
| A61F 13/00 | (2006.01) | |
| A61L 27/50 | (2006.01) | |
| A61L 27/18 | (2006.01) | |
| A61L 27/54 | (2006.01) | |
| A61L 27/56 | (2006.01) | |

(52) U.S. Cl.
CPC .............. *A61L 27/50* (2013.01); *A61L 27/18* (2013.01); *A61L 27/54* (2013.01); *A61L 27/56* (2013.01); *A61L 2300/25* (2013.01); *A61L 2300/414* (2013.01); *A61L 2300/428* (2013.01); *A61L 2300/43* (2013.01); *A61L 2300/45* (2013.01); *A61L 2300/604* (2013.01); *A61L 2400/18* (2013.01)
USPC .......................................... 424/426; 424/422

(58) Field of Classification Search
USPC ........................................................ 424/426
See application file for complete search history.

(56) References Cited

U.S. PATENT DOCUMENTS

2007/0212387 A1  9/2007  Patravale

OTHER PUBLICATIONS

Park et al., "Functional PLGA Scaffold for Induction of Chondrogenesis of Mesenchymal Stem Cell" in 8th World Biomaterials Congress Final Program; May 28-Jun. 1, 2008.*
Machine translation of Han et al. (KR 100654329 B1; published Dec. 8, 2006).*
Chung et al., "Heparin Immobilized Porous PLGA Microspheres for Angiogenic Growth Factor Delivery", Pharmaceutical Research; vol. 23, No. 8, Aug. 2006, pp. 1835-1841.*
Machine translation of Cho (KR 1020070022976 A; published Feb. 28, 2007).*
English translation of Han et al., KR 100654329 B1; published Dec. 8, 2006; translation dated Sep. 2011.*
English translation of Cho et al., KR 1020070022976 A; published Feb. 28, 2007; translation dated Sep. 2011.*
Tscheudschilsuren et al., "Regulation of mesenchymal stem cell and chondrocyte differentiation by MIA", 2006, Experimental Cell Research, vol. 312, pp. 63-72.*
K. Park, et al., "Crossing Frontiers in Biomaterials and Regenerative Medicine", 8th World Biomaterials Congress, May 28-Jun. 1, 2008, 13 Pages.

* cited by examiner

*Primary Examiner* — Michael B Pallay
(74) *Attorney, Agent, or Firm* — Ladas & Parry LLP

(57) ABSTRACT

The present invention relates to an intelligent porous biodegradable polymer scaffold for in situ tissue regeneration in which two kinds of physiologically active substances having high differentiation potential and biocompatibility are introduced into the polymer scaffold and conjugated to the surface thereof, respectively, and a method for the preparation thereof. Since the intelligent porous biodegradable polymer scaffold exhibits improved biocompatibility and differentiation potential due to the introduction of physiologically active substances capable of efficiently inducing cell proliferation and differentiation into both the surface and the inside thereof, it can directly induce in situ tissue regeneration of the musculoskeletal system from stem cells in a living tissue after transplanting the polymer scaffold and stem cells into a human body without additional in vitro cultivation. Therefore, the intelligent porous biodegradable polymer scaffold according to the present invention can be effectively used in the regeneration of various kinds of tissues and organs including the musculoskeletal system.

37 Claims, No Drawings

POROUS BIODEGRADABLE POLYMER SCAFFOLDS FOR IN SITU TISSUE REGENERATION AND METHOD FOR THE PREPARATION THEREOF The present application claims priority to Korean Patent Application No. 10-2008-118115, filed Nov. 26, 2008, the subject matter of which is incorporated herein by reference in its entirety.

FIELD OF THE INVENTION

The present invention relates to an intelligent porous biodegradable polymer scaffold for in situ tissue regeneration in which two different kinds of physiologically active substances having high differentiation potential and biocompatibility are introduced into the inside of the polymer scaffold and conjugated to the surface thereof, respectively, and a method for the preparation thereof.

BACKGROUND OF THE INVENTION

Tissue engineering is a new field that has developed with the progress of science and involves concepts and techniques from various fields of sciences, such as life science, engineering, medical science, and the like. Tissue engineering aims to understand the relationship between the structure and function of body tissues and produce a biological substitute for damaged body tissues or organs for transplantation purposes so as to maintain, improve or restore the function of human body.

A representative tissue engineering technique can be summarized as follows: removing the target tissue from a patient body; isolating cells from the removed tissue; culturing the isolated cells to allow sufficient proliferation; seeding the cells in a biodegradable porous polymer scaffold; culturing the cells in vitro for a predetermined period; and transplanting the obtained hybrid-type cell/polymer structure into the human body. After the transplantation, oxygen and nutrients are provided to the transplanted cells in the biodegradable porous polymer due to the diffusion of body fluids until blood vessels are newly formed. When the blood vessels are formed and blood is provided to the cells, the cells proliferate and differentiate, forming new tissues and organs, while the polymer scaffold is degraded and eventually disappears.

Thus, for such tissue engineering research, it is important to prepare a biodegradable porous polymer scaffold that is similar to body tissue. In order to be used as a raw material for the polymer scaffold, the material should properly serve as a matrix or frame so that tissue cells adhere to the surface of the material and form a new tissue having a three-dimensional structure. It should also be capable of serving as a middle barrier positioned between the transplanted cells and the host cells. This means that the material should be non-toxic and biocompatible such that neither blood coagulation nor an inflammatory reaction occurs after transplantation.

In addition, a polymer scaffold that is eventually completely degraded in vivo while the new tissue is being formed, such as a biodegradable polymer is an attractive candidate for a scaffolding material. Biodegradable polymers, which are currently widely being used, include polyglycolic acid (PGA), poly(L-lactic acid) (PLLA), poly(D,L-lactic acid) (PDLLA), poly(lactic-co-glycolic acid) copolymer (PLGA), poly(ε-caprolactone) (PCL), polyamino acid, polyanhydride, polyorthoester and their copolymers. However, only PGA, PLLA and PLGA have been approved by the U.S. Food & Drug Administration (FDA) as biodegradable polymers which may be used in human bodies and are used as raw materials for preparing a biodegradable porous polymer scaffold for tissue regeneration within a human body.

Various methods for preparing a porous polymer scaffold have been developed, including salt leaching, gas foaming, gas foaming salt method, fiber extrusion and fabric forming, liquid-liquid phase separation, emulsion freeze-drying, electrospinning, three-dimensional printing and the like. For example, the combination of salt leaching and phase separation involves: preparing a solvent mixture by mixing a solvent capable of dissolving a biodegradable polymer with a non-solvent which is incapable of dissolving the biodegradable polymer but is miscible with the above solvent; dissolving the biodegradable polymer in the solvent mixture; and adding an effervescent mixture to generate porosity thereto, thereby preparing a polymer mixture. The thus prepared porous biodegradable polymer scaffold has several advantages, i.e., its specific surface area and porosity are high, it is easy to regulate its pore size, it has an open pore structure, and there is no pore blockage at the surface, resulting in a more efficient introduction of stem cells into the scaffold. However, when transplanted into a living body, it is difficult to differentiate the stem cells into a specific target cell due to the absence of physiologically active substances that induce tissue regeneration.

Recently, various attempts have been made to introduce a physiologically active substance, such as growth factors or ligand peptides, into polymer scaffolds in order to improve the differentiation potential of stem cells. For instance, methods of activating stem cells by using growth factors (T. Motoki et al., *Cell and Tissue Research* 285: 205, 1996), methods of releasing a growth factor through gas foaming/salt leaching (J. J. Yoon et al., *Biosubstances* 24: 2323, 2003), and methods of stimulating the formation of bone tissue by using a porous gelatin microparticle (Z. S. Patel et al., *Bone* 43: 931, 2008) have been reported.

However, the above methods are problematic in that the fabrication process is relatively complicated, there is a risk of transformation of the porous biodegradable polymer scaffold taking place when its surface is modified via polymer pyrolysis, and the differentiation potential and biocompatibility are significantly reduced during the tissue regeneration of stem cells into the specific target tissue.

In order to overcome these problems, the present inventors previously developed a porous polymer scaffold with improved biocompatibility in which a peptide ligand or a growth factor is conjugated to the surface thereof (Korean Patent No. 54329). However, since in the above porous polymer scaffold, a single kind of physiologically active substance is conjugated only to the surface thereof, it is necessary for the above porous polymer scaffold to undergo in vitro cultivation with stem cells in a differentiation medium containing an additional physiologically active substance for a predetermined period, and then, transplant it in a cell/polymer construct form under partially differentiated conditions. Namely, the above porous polymer scaffold had problems in that it cannot directly induce tissue regeneration of new tissues or organs from stem cells in a living body.

Therefore, the present inventors have developed a method of efficiently inducing in situ tissue regeneration of the musculoskeletal system by using a porous biodegradable polymer scaffold in a living body, and found that when two different kinds of physiologically active substances capable of improving differentiation potential and biocompatibility are introduced into both the surface and the interior of the polymer scaffold, the thus prepared porous biodegradable polymer scaffold can efficiently induce in situ tissue regeneration of the musculoskeletal system from stem cells without in vitro cultivation with the stem cells before transplantation.

SUMMARY OF THE INVENTION

One of the objectives of the present invention is to provide an intelligent porous biodegradable polymer scaffold capable of directly inducing in situ tissue regeneration of the musculoskeletal system from stem cells by transplantation with the stem cells in a living body, making it unnecessary to transplant in the form of a cell/polymer hybrid construct after the stem cells are inoculated into the polymer scaffold and undergo in vitro cultivation for a predetermined period.

In order to achieve the above objective, one embodiment of the present invention relates to an intelligent porous biodegradable polymer scaffold for in situ tissue regeneration of the musculoskeletal system where the surface of the polymer scaffold is modified with a carboxyl group-containing hydrophilic monomer, a first physiologically active substance is introduced into the interior of the polymer scaffold, and a second physiologically active substance is conjugated to the surface thereof by using heparin fixed to the hydrophilic monomer as a linker.

Another embodiment of the present invention relates to a method of preparing the above intelligent porous biodegradable polymer scaffold comprising:
1) preparing a polymer solution by mixing a biodegradable polymer, an effervescent mixture of carbonate and an organic acid and a first physiologically active substance in a solvent, followed by evaporation of the solvent from the polymer solution, to thereby obtain a polymer sample in which the first physiologically active substance is introduced into the inside of the polymer sample;
2) effervescing the polymer sample by soaking it in an alcohol aqueous solution and drying the same, to obtain a porous biodegradable polymer scaffold;
3) treating the porous biodegradable polymer scaffold with plasma with a reactive gas, followed by graft-polymerization with a carboxyl group-containing monomer on the surface thereof, to thereby modify the hydrophobic surface of the polymer scaffold to hydrophilic;
4) activating the carboxyl group graft-polymerized onto the surface of the porous biodegradable polymer scaffold and immobilizing heparin on the activated carboxyl group; and
5) conjugating a second physiologically active substance to the heparin fixed on the surface of the porous biodegradable polymer scaffold.

DETAILED DESCRIPTION OF THE INVENTION

The present invention provides an intelligent porous biodegradable polymer scaffold for in situ tissue regeneration of the musculoskeletal system in which the surface of the polymer scaffold is modified with a carboxyl group-containing hydrophilic monomer, a first physiologically active substance is introduced into the inside of the polymer scaffold, and a second physiologically active substance is conjugated to the surface thereof by using heparin immobilized on the hydrophilic monomer as a linker.

Since the intelligent porous biodegradable polymer scaffold of the present invention exhibits improved biocompatibility and differentiation potential due to the introduction of two different physiologically active substances capable of inducing cell proliferation and differentiation in both the surface and inside thereof, it can directly induce in situ tissue regeneration of the musculoskeletal system from stem cells in a living tissue.

As a biodegradable polymer suitable for the intelligent porous biodegradable polymer scaffold according to the present invention, any polymer may be used for the present invention, so long as it is capable of being degraded in a living body. Suitable examples of the biodegradable polymer include, but are not limited to, polyglycolic acid (PGA), polylactic acid (PLA), polylactic acid-glycolic acid copolymer (PLGA), poly-ε-caprolactone (PCL), polyamino acid, polyanhydride, polyorthoester, derivatives, copolymers and mixtures thereof. PLA, PGA, PLGA copolymer and mixtures thereof that have been approved by FDA as potential candidates for tissue regeneration may be used. There is no limitation on the molecular weight of the biodegradable polymer used, but, for example, a biodegradable polymer having a weight average molecular weight ($M_w$) ranging from 5,000 to 2,000,000 may be used.

The carboxyl group-containing hydrophilic monomers suitable for the surface modification in the intelligent porous biodegradable polymer scaffold according to the present invention include carboxylic acids having an unsaturated group at its terminal group such as acrylic acid, methacrylic acid, maleic acid, itaconic acid, aconitic acid and the like, and mixtures thereof. In some embodiments, the carboxyl group-containing hydrophilic monomer may be modified to the surface of the porous biodegradable polymer scaffold in a molar ratio of 100:1 to 500:1.

As a first physiologically active substance suitable for the introduction into the inside of the intelligent porous biodegradable polymer scaffold according to the present invention, any substance may be used for the present invention, so long as it is capable of inducing tissue regeneration of the musculoskeletal system and has high differentiation potential and biocompatibility. Suitable examples thereof include, but are not limited to, dexamethasone, β-glycerophosphate, ascorbate-2-phosphate, ascobate, demineralized bone matrix (DBM), hydroxyapatite (HAP), ascorbic acid, 1,25-dihydroxyvitamin $D_3$, tricalciumphosphate (TCP), collagen, parathyroid hormone (PTH), PTH 1-34 peptide, retinoic acid-sensitive protein (CD-RAP) and the like. Further, the first physiologically active substances suitable for the present invention include biocompatible ligand peptides and growth factors capable of inducing in vivo differentiation of stem cells into musculoskeletal cells. Suitable examples of such a ligand peptide include Arg-Gly-Asp (RGD), Arg-Glu-Asp-Val (REDV), Leu-Asp-Val (LDV), Tyr-Ile-Gly-Ser-Arg (YIGSR), Pro-Asp-Ser-Gly-Arg (PDSGR), Ile-Lys-Val-Ala-Val (IKVAV), Arg-Asn-Ile-Ala-Glu-Ile-Ile-Lys-Asp-Ala (RNIAEIIKDA) and the like, but are not limited thereto. RGD and PDSGR improve cell adhesiveness to all kinds of cell types, while REDV and LDV promote the proliferation of vascular endothelial cells. YIGSR promotes the proliferation of vascular cells, while IKVAV and RNIAEIIKDA promote that of nerve cells. Further, suitable examples of such growth factors include transforming growth factor-β (TGF-β), insulin-like growth factor (IGF), epidermal growth factor (EGF), neuron growth factor (NGF), vascular endothelial growth factor (VEGF), fibroblast growth factor (FGF), hepatocyte growth factor (HGF), platelet-derived growth factor (PDGF), bone morphogenetic protein (BMP), growth differentiation factor (GDF) and the like, but are not limited thereto.

In the intelligent porous biodegradable polymer scaffold according to the present invention, heparin is fixed to the surface of the polymer scaffold by forming a covalent bond with an activated carboxyl group of the hydrophilic monomer graft-polymerized onto the surface of the polymer scaffold. The thus fixed heparin is used as a linker for conjugating the second physiologically active substance for improving proliferation potential and biocompatibility to the surface of the porous biodegradable polymer scaffold. Heparin suitable for the present invention may be natural heparin, recombinant heparin or heparin derivatives, and may be fixed to the surface of the polymer scaffold in a molar ratio of 100:1 to 500:1. If the molar ratio of heparin to the polymer scaffold is too low, there is the risk of the amount of the second physiologically active substance being conjugated to the surface thereof decreasing. On the other hand, if its molar ratio is too high, the excessive amount of heparin interferes with normal blood coagulation.

The second physiologically active substance can be conjugated to the surface of the porous biodegradable polymer scaffold by using the heparin fixed to the surface thereof as a linker. The second physiologically active substance may be conjugated in the amount of 0.01 to 50 nmol based on 1 g of the porous biodegradable polymer scaffold. If the molar ratio of the physiologically active substance to the polymer scaffold is too low or too high, tissue regeneration of the musculoskeletal system may be not effectively induced.

As the second physiologically active substance suitable for the present invention, any substance may be used for the present invention, so long as it is capable of inducing tissue regeneration of the musculoskeletal system and has high differentiation potential and biocompatibility. Suitable examples thereof include, but are not limited to, dexamethasone, β-glycerophosphate, ascorbate-2-phosphate, ascobate, demineralized bone matrix (DBM), hydroxyapatite (HAP), ascorbic acid, 1,25-dihydroxyvitamin $D_3$, tricalciumphosphate (TCP), collagen, parathyroid hormone (PTH), PTH 1-34 peptide, retinoic acid-sensitive protein (CD-RAP) and the like. Further, the second physiologically active substances suitable for the present invention include biocompatible ligand peptides and growth factors capable of inducing in vivo differentiation of stem cells into musculoskeletal cells. Descriptions regarding suitable examples of such ligand peptides and growth factors already described above are not necessarily repeated herein. The second physiologically active substance conjugated to the surface of the porous biodegradable polymer scaffold according to the present invention may be different from the first physiologically active substance incorporated into the inside thereof.

The intelligent porous biodegradable polymer scaffold according to the present invention has a pore size in the range of 10 to 500 μm, a specific surface area per unit volume in the range of 100 to 500 $cm^3$/g, and a porosity in the range of 90 to 98%.

Since the intelligent porous biodegradable polymer scaffold exhibits improved biocompatibility and differentiation potential due to the introduction of two different physiologically active substances capable of inducing cell proliferation and differentiation into both the surface and the inside thereof, it can directly induce in situ tissue regeneration of the musculoskeletal system from stem cells in a living tissue after transplanting the polymer scaffold and stem cells into a human body. In order to induce tissue regeneration of the musculoskeletal system, a conventional polymer scaffold is first inoculated with stem cells and cultured in vitro for a certain period of time, to thereby prepare a hybrid construct of the polymer scaffold and stem cells, and then, the thus prepared hybrid construct is transplanted into a living body. In contrast, the intelligent porous biodegradable polymer scaffold according to the present invention can directly induce in situ tissue regeneration in a living tissue, which means although it is transplanted with stem cells into a living body without in vitro cultivation, the physiologically active substances introduced into the surface and the inside of the polymer scaffold effectively induce proliferation and differentiation of the stem cells at the transplantation site, resulting in effective tissue regeneration of the musculoskeletal system. The intelligent porous biodegradable polymer scaffold according to the present invention is the first polymer scaffold including physiologically active substances at both the surface and the inside thereof, and thereby capable of efficiently inducing in situ tissue regeneration of the musculoskeletal system in a living body.

Further, since the intelligent porous biodegradable polymer scaffold according to the present invention exhibits a uniform pore size, a high specific surface area per unit volume and a high porosity as well as improved biocompatibility and differentiation potential, it can be effectively used in the regeneration of various types of tissues and organs including the musculoskeletal system from stem cells.

The intelligent porous biodegradable polymer scaffold for in situ tissue regeneration according to the present invention as described above can be prepared by a method involving:

1) preparing a polymer solution by mixing a biodegradable polymer, an effervescent mixture of carbonate and an organic acid and a first physiologically active substance in a solvent, followed by evaporation of the solvent from the polymer solution, to thereby obtain a polymer sample in which the first physiologically active substance is introduced into the inside of the polymer sample;

2) effervescing the polymer sample by soaking it in an alcohol aqueous solution and drying the same, to obtain a porous biodegradable polymer scaffold;

3) treating the porous biodegradable polymer scaffold with plasma with a reactive gas, followed by graft-polymerization with a carboxyl group-containing monomer on the surface thereof, to thereby modify the hydrophobic surface of the polymer scaffold into hydrophilic;

4) activating the carboxyl group graft-polymerized onto the surface of the porous biodegradable polymer scaffold and immobilizing heparin on the activated carboxyl group; and 5) conjugating a second physiologically active substance to the heparin fixed on the surface of the porous biodegradable polymer scaffold.

In step 1), a polymer solution is prepared by mixing a biodegradable polymer, an effervescent mixture of carbonate and an organic acid and a first physiologically active substance in a solvent. Here, 4.5 to 15% wt of the polymer scaffold, 80 to 95% wt of the effervescent mixture and 0.0001 to 5% wt of the first physiologically active substance are added to 5 to 50% wt of the solvent based on the total weight of the polymer solution.

The above step 1) is characteristic of the preparation method according to the present invention. In contrast to the conventional methods of preparing a porous biodegradable polymer scaffold which prepare a polymer solution by mixing a biodegradable polymer and an effervescent mixture in a solvent, the method of the present invention employs a physiologically active substance having a high differentiation potential and biocompatibility together with the above ingredients to prepare a polymer solution, which makes the physiologically active substance introduced into the inside of the polymer scaffold. Such introduction of a physiologically active substance into the polymer scaffold makes a more efficient induction of in situ tissue regeneration possible.

Descriptions regarding suitable examples of such biodegradable polymers already described above are not necessarily repeated herein. There is no limitation on the molecular weight of the biodegradable polymer used, although it is preferable to use a biodegradable polymer having a weight average molecular weight ($M_w$) ranging from 5,000 to 2,000,000.

The effervescent mixture used in the formation of pores in step 1) is a mixture of carbonate and an organic acid in a volume ratio of 1:1 to 1:3, the carbonate and organic acid being pharmacologically acceptable, nontoxic and high water-soluble, and having a uniform particle size. The carbonates suitable for the present invention include any carbonate capable of generating carbon dioxide, which may be exemplified by sodium bicarbonate, sodium carbonate, ammonium bicarbonate, ammonium carbonate, potassium bicarbonate, potassium carbonate, calcium carbonate and the like. Further, the organic acids suitable for the present invention include citric acid, tartaric acid, succinic acid, maleic acid, fumaric acid, malonic acid, malic acid, gluconic acid, mucic acid, amino acids and the like. If the effervescent mixture is a mixture of carbonate and an organic acid having a different particle size, it is possible to prepare a porous biodegradable polymer scaffold having a dual pore structure where relatively small size pores and relatively large size pores are formed together.

Descriptions regarding suitable examples of such first physiologically active substances already described above are not necessarily repeated herein.

The solvents suitable for the preparation of a polymer solution in step 1) may be a solvent capable of dissolving a biodegradable polymer alone, or a mixture of the solvent with a non-solvent which cannot dissolve the biodegradable polymer but is miscible with the solvent. In case of using a solvent capable of dissolving a biodegradable polymer alone, when the thus prepared polymer solution is effervesced and dried, a porous biodegradable polymer scaffold having a single pore structure is obtained. On the other hand, in case of using a mixture of the solvent with the non-solvent which cannot dissolve the biodegradable polymer but is miscible with the solvent, when the thus prepared polymer solution is effervesced and dried, a porous biodegradable polymer scaffold having a dual pore structure is obtained. That is, it is possible to regulate the pore structure of the porous biodegradable polymer scaffold by selecting a solvent system for the preparation of a polymer solution.

Suitable examples of solvents capable of dissolving a biodegradable polymer include methylene chloride, chloroform, dichloromethane, acetone, dioxane, tetrahydrofuran, mixtures thereof, but are not limited thereto. Suitable examples of the non-solvent which cannot dissolve the biodegradable polymer but is miscible with the solvent include water, ethanol, methanol, acetone, mixtures thereof, but are not limited thereto. When the solvent and non-solvent are used in a mixture, the solvent and non-solvent may be mixed in a volume ratio of 80:20 to 95:5.

The thus prepared polymer solution is left alone at a temperature of −196° C. to room temperature for 1 to 24 hours so as to evaporate off the solvent, to thereby obtain a polymer sample where the first physiologically active substance having a high proliferation potential and biocompatibility is introduced into the inside thereof.

In step 2), the polymer sample obtained in step 1) is soaked in an aqueous alcohol solution to effervesce, followed by drying, to thereby prepare a porous biodegradable polymer scaffold. The aqueous alcohol solution suitable for the present invention may be a mixture of water and alcohol, such as ethanol, methanol, isopropanol and mixtures thereof, in a volume ratio of 50:50 to 70:30. The polymer sample obtained in step 1) is soaked in the aqueous alcohol solution and subjected to effervescence by evolving carbon dioxide gas in combination with a physical method such as ultrasonic waves, microwave and agitation. After the effervescence is completed, when the polymer sample is dried, a porous biodegradable polymer scaffold having an interconnected pore structure both on the surface and inside can be obtained. Depending on the use of a single solvent, the combination use of a solvent and a non-solvent, the use of a effervescent mixture having a different particle size and the like during the preparation of a polymer sample in step 1), the porous biodegradable polymer scaffold obtained in step 2) may have a single pore structure where pores having a uniform size are distributed on the whole polymer scaffold, or a dual pore structure where relatively large pores are distributed on the whole polymer scaffold and relatively small pores are formed on the walls connecting the large pores.

The preparation of a porous biodegradable polymer scaffold according to the above steps 1) and 2) has several advantages over the conventional methods such as salt leaching, phase separation, emulsion freeze-drying and the like: (i) it can prepare a polymer scaffold in a more simple manner; (ii) it can easily control the pore size of the polymer scaffold; (iii) it can form an open pore structure with a high surface area and porosity, and there is no pore blockage at the surface and secretion of remnant toxic substances. The porous biodegradable polymer scaffold obtained in step 2) has a pore size in the range of 10 to 500 µm, a specific surface area per unit volume in the range of 100 to 500 $cm^3/g$ and a porosity in the range of 90 to 98%. Further, since the physiologically active substances having high proliferation potential and biocompatibility are introduced into the inside of the porous biodegradable polymer scaffold according to the present invention for efficient tissue regeneration induction of the musculoskeletal system, there is no need to transplant in the form of a cell/polymer hybrid construct after stem cells are inoculated into the polymer scaffold and subjected to in vitro cultivation for a predetermined period. Instead, although it is transplanted with stem cells into a living body without in vitro cultivation, the porous biodegradable polymer scaffold according to the present invention can effectively induce proliferation and differentiation of the stem cells in a living tissue, resulting in direct in situ tissue regeneration of the musculoskeletal system at the transplantation site.

In step 3), the porous biodegradable polymer scaffold obtained in step 2) is subjected to surface plasma treatment with a reactive gas and graft polymerization with a carboxyl group-containing hydrophilic monomer. In this step, the reactive gas suitable for the surface plasma treatment includes helium (He), argon (Ar), nitrogen ($N_2$), oxygen ($O_2$), hydrogen ($H_2$), carbon dioxide ($CO_2$), carbon monoxide (CO), ammonia ($NH_3$), $H_2O$, mixtures thereof and the like, but are not limited thereto. The surface plasma treatment using such a reactive gas is carried out at a power of 10 to 100 $W/cm^2$ for 30 to 300 seconds under pressures of 10 to 300 mtorr. Any plasma source known in the art, including radio frequency (RF) power, medium frequency (MF) power, direct current (DC) power, microwave (MW) power and the like, may be used in this surface plasma treatment, so long as it is capable of generating plasma. As a result of the above surface plasma treatment, the hydrophobic surface of the porous biodegradable polymer scaffold is modified to be hydrophilic.

Next, a carboxyl group (—COOH)-containing hydrophilic monomer is graft-polymerized to the thus hydrophilically modified surface of the porous biodegradable polymer scaffold. Descriptions regarding suitable examples of such carboxyl group-containing hydrophilic monomers already described above are not necessarily repeated herein. Here, the carboxyl group-containing hydrophilic monomer may be graft-polymerized to the porous biodegradable polymer scaffold in a molar ratio of 100:1 to 500:1. If the molar ratio of the carboxyl group-containing hydrophilic monomer to the porous biodegradable polymer scaffold is too low, there is a possibility of the hydrophilic monomer not being sufficiently graft-polymerized onto the inside of the polymer scaffold. On the other hand, if the molar ratio of the carboxyl group-containing hydrophilic monomer to the porous biodegradable polymer scaffold is too high, there is a problem in that an excessive amount of carboxyl group would be graft-polymerized onto the surface thereof. In case of using acrylic acid as a carboxyl group-containing hydrophilic monomer, graft polymerization may be performed directly in a plasma chamber. On the other hand, in case of using the other carboxyl group-containing hydrophilic monomers listed above except for acrylic acid, graft polymerization may be performed in an aqueous solution after the polymer scaffold is pre-treated with plasma so as to form radicals on the surface thereof and stabilized in the air.

In step 4), the porous biodegradable polymer scaffold where the carboxyl group-containing hydrophilic monomers are graft-polymerized onto the surface thereof in step 3) is soaked in a buffer solution at a temperature of 4 to 37° C. for 30 minutes to 24 hours in the presence of a coupling agent, to thereby activate the carboxyl groups. Examples of the buffer solution suitable for the above activation step include 2-morpholinoethane sulfonic acid (MES), propanesulfonic acid (MOPS), triethylene amine and the like, and those of the coupling agent include 1-ethylene-3-(3-dimethylamino-propyl)carbodiimide (EDC), N-hydroxyl-succinimide (NHC), N,N-dicyclohexylcarbodiimide (DCC), bis(2-oxo-3-oxazolidinyl)phosphinic chloride (BOP-Cl), disuccinimidyl carbonate (DSC), N,N-diisopropylcarboimide (DIPC), 4-(p-azidosalicylamido)-butylamine (ASBA) and the like, but are not limited thereto.

When the carboxyl groups graft-polymerized onto the surface of the porous biodegradable polymer scaffold are activated according to the above step, heparin is immobilized on the surface thereof by forming a covalent bond between the activated carboxyl group and an amine group of heparin. The thus immobilized heparin is used as a linker for conjugating the physiologically active substance capable of improving proliferation potential and biocompatibility to the surface of the porous biodegradable polymer scaffold in the following steps. As compared with the direct conjugation of a physiologically active substance to the surface of the polymer scaffold without heparin, when a physiologically active substance is conjugated to the surface thereof by using heparin as a linker according to the present invention, the physiologically active substance is endowed with flexibility due to the use of heparin. Therefore, if the above polymer scaffold is transplanted into the body, the physiologically active substances conjugated to the surface more efficiently interact with adjacent cell membrane receptors. Further, it is possible to introduce various kinds of physiologically active substances into the polymer scaffold by using a functional group of heparin.

Heparin suitable for the present invention may be natural heparin, recombinant heparin or heparin derivatives, and may be fixed to the surface of the polymer scaffold in a molar ratio of 100:1 to 500:1. If the molar ratio of heparin to the polymer scaffold is too low, there is a risk of decreasing the amount of the second physiologically active substance being conjugated to the surface thereof. On the other hand, if its molar ratio is too high, the excessive amount of heparin interferes with normal blood coagulation.

The immobilization of heparin on the surface of the porous biodegradable polymer scaffold by using the activated carboxyl groups in step 4) can be omitted in the case of introducing a ligand peptide into the surface of the polymer scaffold as the second physiologically active substance in the following step 5). Since the ligand peptide can directly form a chemical covalent bond with the carboxyl group at the surface of the porous biodegradable polymer scaffold, it can be simply and directly introduced into the polymer scaffold without the use of heparin as a linker.

In step 5), the second physiologically active substance having high proliferation potential and biocompatibility is conjugated to the surface of the porous biodegradable polymer scaffold by using heparin immobilized thereon as a linker. The porous biodegradable polymer scaffold where heparin is immobilized on the surface is soaked in a buffer solution in which the second physiologically active substance capable of improving proliferation potential and biocompatibility is dissolved at a temperature of 4 to 30° C. for 1 to 24 hours. Here, it is preferable to conjugate the second physiologically active substance in the amount of 0.01 to 50 nmol based on 1 g of the porous biodegradable polymer scaffold. If the molar ratio of the physiologically active substance to the polymer scaffold is too low or too high, tissue regeneration of the musculoskeletal system may be not effectively induced.

Descriptions regarding suitable examples of such second physiologically active substances already described above are not necessarily repeated herein. The second physiologically active substance conjugated to the surface of the porous biodegradable polymer scaffold in this step is preferably different from the first physiologically active substance incorporated into the inside thereof in step 1).

As described above, the method of the present invention can prepare an intelligent porous biodegradable polymer scaffold where two different kinds of the physiologically active substance are introduced into both the surface and inside thereof. The intelligent porous biodegradable polymer scaffold according to the present invention can be effectively used in the regeneration of various kinds of tissues and organs including the musculoskeletal system from stem cells.

EXAMPLES

Hereinafter, the embodiments of the present invention will be described in more detail with reference to the following examples. However, the examples are only provided for purposes of illustration and are not to be construed as limiting the scope of the invention.

Example 1

A poly(lactic-co-glycolic acid) copolymer (lactic acid:glycolic acid=50:50 w/w, PLGA) having a molecular weight of about 110,000 was added to a mixture of dioxane and water (85:15 w/v) and uniformly dissolved therein under stirring by using a magnetic stirrer, to thereby obtain a homogenous PLGA solution. An effervescent mixture (10 to 50 μm and 200 to 300 μm in particle size) of sodium bicarbonate and citric acid (3:1 in molar ratio) was added to the PLGA solution so that the weight ratio of the effervescent mixture to the PLGA solution was 20:1. Then, dexamethasone as a physiologically active substance was added thereto at a final concentration of 0.5% wt and uniformly mixed therein. The resulting solution was poured into a frame made of silicone, having a shape of a donut having a diameter of 8 mm, followed by leaving it alone for 30 minutes to evaporate off the solvent, thereby obtaining a polymer sample having a disk shape. Then, the polymer sample was soaked in a mixed aqueous solution of water and ethanol (50:50 w/w) and subjected to foaming for 2 hours after undergoing ultrasonication for 30 seconds. After the foaming stage, the polymer sample was taken out and freeze-dried for 24 hours, thereby obtaining a biodegradable dual pore polymer scaffold where dexamethasone was introduced into the inside thereof.

Next, for the surface modification of a polymer scaffold, the thus obtained biodegradable dual pore polymer scaffold was treated with argon plasma so as to activate its surface, and acrylic acid was graft-polymerized onto the activated surface, modifying the hydrophobic surface of the polymer scaffold to be hydrophilic. The hydrophilic polymer scaffold was then treated with EDC (1-ethylene-3-(3-dimethylamino-prophyl) carbodiimide) and NHC (N-hydroxyl-succinimide), to thereby activate carboxyl groups of the acrylic acid graft-polymerized onto the surface of the polymer scaffold. Subsequently, it was soaked in a MES solution (pH 5.6) containing heparin at a concentration of 1% wt at 4° C. for 2 hours so that heparin immobilized on the activated carboxyl group. The polymer scaffold was taken out and soaked in a PBS solution (pH 7.4) supplemented with 150 ng/ml of TGF-β1 at 37° C. for 2 hours, to thereby prepare an intelligent porous biodegradable polymer scaffold where TGF-β1 was conjugated to heparin immobilized on the surface thereof.

As a result of analysis using scanning electron microscopy (SEM), it has been found that the thus prepared intelligent porous biodegradable polymer scaffold has a dual pore structure whose pore shape and distribution were almost the same through the outer surface and inner section, and the size of small pores is in the range of 10 to 50 μm, while the large pores have a size in the range of 200 to 300 μm. Further, it has been discovered that the intelligent porous biodegradable polymer scaffold of the present invention has a consecutive open pore structure having high interconnectivity between the pores without pore blockage at the outer surface.

The results of electron spectroscopy for chemical analysis (ESCA) and energy dispersive spectrometer (EDAX) analysis showed that dexamethasone is introduced inside the dual pore structure of the intelligent porous biodegradable polymer scaffold according to the present invention. Further, the results of ELISA (enzyme-linked immunosorbent assay) showed that TGF-β1 is conjugated to the surface of the polymer scaffold.

As a result of examining cell differentiation behavior by using bone marrow stem cells, it has been found that the intelligent porous biodegradable polymer scaffold of the present invention in which the physiologically active substances are introduced into both the surface and the inside thereof shows superior differentiation potential into chondrocytes over a polymer scaffold having no physiologically active substance (Comparative Example 1) and a polymer scaffold in which the physiologically active substance is introduced into only the surface thereof (Comparative Example 2).

Further, in order to investigate the effect of the intelligent porous biodegradable polymer scaffold of the present invention on in situ tissue regeneration, bone marrow stem cells were inoculated thereon, followed by immediately transplanting into the subcutaneous tissue of a nude mouse. Four weeks later, the polymer scaffold was extracted from the transplantation site. As a result of analyzing the extracted polymer scaffold with SEM, it has been found that cells differentiated from the bone marrow stem cells are even distributed on the inside of the porous biodegradable polymer scaffold according to the present invention as well as the surface thereof.

In addition, in order to examine whether the cells differentiated from the stem cells on the extracted polymer scaffold are chondrocytes, the expression of type II collagen as a specific marker for chondrocytes was analyzed with RT-PCR (reverse transcription polymerase chain reaction). As a result, it has been found that the expression of type II collagen is increased in the differentiated cells. These results demonstrated that since the intelligent porous biodegradable polymer scaffold of the present invention contains the physiologically active substances in both the surface and the inside thereof, it can more efficiently induce in situ tissue regeneration of the musculoskeletal system in a living tissue.

Example 2

According to the same method as described in Example 1, the porous biodegradable polymer scaffold having a dual pore structure where dexamethasone was introduced into the inside thereof was prepared, subjected to surface plasma treatment and graft-polymerized with acrylic acid onto the surface thereof. Next, a carboxyl group of the acrylic acid was activated, and heparin was immobilized on the activated carboxyl group. The thus prepared porous biodegradable polymer scaffold was soaked in a PBS solution (pH 7.4) supplemented with 200 ng/ml of BMP-2 (member of bone morphogenic proteins) at 37° C. for 2 hours, to thereby obtain an intelligent porous biodegradable polymer scaffold in which BMP-2 was conjugated to the heparin immobilized on the surface of the polymer scaffold.

The results of SEM analysis showed that the intelligent porous biodegradable polymer scaffold of the present invention has a dual pore structure where the pore shape and distribution are almost identical at the outer surface and inner cross-section of the scaffolds, and the size of large pores is in the range of 200 to 300 μm, while the small pores have a size in the range of 10 to 50 μm. As a result of ESCA, EDAX and ELISA analyses, it has been found that dexamethasone is introduced inside the dual pore structure of the intelligent porous biodegradable polymer scaffold, and BMP-2 is conjugated to the surface thereof. As a result of examining cell differentiation behavior by using adipose-derived stem cells, it has been found that the intelligent porous biodegradable polymer scaffold of the present invention in which the physiologically active substances are introduced into both the surface and the inside thereof shows superior differentiation potential into chondrocytes over a polymer scaffold having no physiologically active substance (Comparative Example 1) and a polymer scaffold in which the physiologically active substance is introduced into only the surface thereof (Comparative Example 2).

Further, the intelligent porous biodegradable polymer scaffold of the present invention was inoculated with adipose-derived stem cells, transplanted immediately into the subcutaneous tissue of a nude mouse, and then, cell differentiation was induced for 4 weeks. As a result, it has been found that cells differentiated from the adipose-derived stem cells are distributed through the inside of the polymer scaffold as well as the surface thereof, and the thus differentiated cells are chondrocytes. These results demonstrated that since the intelligent porous biodegradable polymer scaffold of the present invention contains the physiologically active substances in both the surface and the inside thereof, it can more efficiently induce in situ tissue regeneration of the musculoskeletal system in a living tissue.

Example 3

Poly (L-lactic acid) (PLLA) having a molecular weight of about 100,000 was dissolved in methylene chloride to obtain a 5% wt of PLLA solution. An effervescent mixture (200 to 300 μm of particle size) of sodium carbonate and citric acid (3:1 in molar ratio) was added to the PLLA solution so that the weight ratio of the effervescent mixture to the PLLA solution was 5:1. To the resulting solution was added β-glycerophosphate at a final concentration of 1% wt and homogeneously mixed, to thereby obtain a polymer solution. The polymer solution was poured into a frame made of silicone, having a shape of a donut with a diameter of 8 mm, followed by leaving it alone for 30 minutes to evaporate off the solvent, thereby obtaining a polymer sample having a disk shape. Then, the polymer sample was soaked in a mixed aqueous solution of water and ethanol (50:50 w/w) and subjected to foaming for 2 hours after undergoing ultrasonication for 30 seconds. After the foaming stage, the polymer sample was taken out and vacuum-dried at 40° C. for 2 hours, thereby providing a biodegradable single pore polymer scaffold in which β-glycerophosphate was introduced into the inside thereof.

The surface of the polymer scaffold obtained above was activated by treating with oxygen plasma, followed by graft-polymerization with methacrylic acid, which makes the hydrophobic surface of the polymer scaffold modified into hydrophilic due to the introduction of a carboxyl group into the surface thereof. Next, the polymer scaffold was soaked in a MES solution (pH 5.6) supplemented with heparin (1% wt) at 4° C. for 2 hours so that the carboxyl group of methacrylic acid graft-polymerized onto the surface of the polymer scaffold was activated simultaneously while immobilizing heparin on the activated carboxyl group. The resulting polymer scaffold was taken out and soaked again in a PBS solution (pH 7.4) supplemented with 200 ng/ml of BMP-2 at 37° C. for 2 days, to thereby obtain an intelligent single pore biodegradable polymer scaffold where BMP-2 was conjugated to the heparin immobilized on the surface thereof.

The results of SEM analysis showed that the intelligent porous biodegradable polymer scaffold of the present invention has a highly interconnected pore structure where single pores having a size in the range of 200 to 300 μm are even distributed at both the outer surface and inside of the polymer scaffold, and there is no pore blockage at the outer surface. As a result of ESCA, EDAX and ELISA analyses, it has been found that β-glycerophosphate is introduced inside the dual pore structure of the intelligent porous biodegradable polymer scaffold, and BMP-2 is conjugated to the surface thereof. As a result of examining cell differentiation behavior by using cord blood stem cells, it has been found that the intelligent porous biodegradable polymer scaffold of the present invention in which the physiologically active substances are introduced into both the surface and the inside thereof shows higher expression level of type I collagen as a specific marker for chondrocytes and differentiation potential into chondrocytes than a polymer scaffold having no physiologically active substance (Comparative Example 1) or a polymer scaffold in which the physiologically active substance is introduced into only the surface thereof (Comparative Example 2).

Example 4

To a PCL solution in which poly-ε-caprolactone (PCL) having a molecular weight of about 100,000 is dissolved in tetrahydrofuran at a concentration of 10% wt, an effervescent mixture (10 to 50 μm and 300 to 400 μm of particle size) of ammonium bicarbonate and succinic acid (3:1 in molar ratio) was added so that the weight ratio of the effervescent mixture to the PCL solution was 85:15, followed by uniformly mixing with demineralized bone matrix (DBM) at a concentration of 1% wt, to thereby obtain a polymer solution. The polymer solution was poured into a frame made of silicone, having a shape of a donut with a diameter of 8 mm, followed by leaving it alone for 30 minutes to evaporate off the solvent, thereby obtaining a polymer sample having a disk shape. The following steps were carried out according to the same method as described in Example 1, to thereby obtain an intelligent dual pore biodegradable polymer scaffold.

The results of SEM analysis showed that the intelligent porous biodegradable polymer scaffold of the present invention has a dual pore structure where the pore shape and distribution are almost identical at the outer surface and inner cross-section of the scaffolds, and the size of large pores is in the range of 200 to 300 μm, while the small pores have a size in the range of 10 to 50 μm. As a result of ESCA, EDAX and ELISA analyses, it has been found that DBM is introduced inside the dual pore structure of the intelligent porous biodegradable polymer scaffold, and TGF-β1 is conjugated to the surface thereof.

Further, according to the same method as described in Example 1, the intelligent porous biodegradable polymer scaffold of the present invention was inoculated with adipose-derived stem cells, transplanted immediately into the subcutaneous tissue of a nude mouse, and then, induced cell differentiation for 4 weeks. As a result, it has been found that cells differentiated from the adipose-derived stem cells are distributed through the inside of the polymer scaffold as well as the surface thereof, and the thus differentiated cells are chondrocytes. These results demonstrated that since the intelligent porous biodegradable polymer scaffold of the present invention contains the physiologically active substances in both the surface and inside thereof, it can more efficiently induce in situ tissue regeneration of the musculoskeletal system in a living tissue.

Example 5

To a PCL solution in which poly-ε-caprolactone (PCL) having a molecular weight of about 100,000 is dissolved in tetrahydrofuran at a concentration of 10% wt, an effervescent mixture (100 to 300 μm of particle size) of potassium bicarbonate and fumaric acid (1:1 in molar ratio) was added so that the weight ratio of the effervescent mixture to the PCL solution was 90:10, followed by uniformly mixing with ascorbic acid at a concentration of 2% wt, to thereby obtain a polymer solution. The polymer solution was poured into a frame made of silicone, having a shape of a donut with a diameter of 8 mm, followed by leaving it alone for 30 minutes to evaporate off the solvent, thereby obtaining a polymer sample having a disk shape. Then, the polymer sample was soaked in a mixed aqueous solution of water and ethanol (5:95 w/w) and subjected to foaming for 2 hours after undergoing ultrasonication for 30 seconds. After the foaming stage, the polymer sample was taken out and vacuum-dried at 40° C. for 2 hours to provide a biodegradable single pore polymer scaffold. The following steps were carried out according to the same method as described in Example 3, to thereby obtain an intelligent single pore biodegradable polymer scaffold.

The results of SEM analysis showed that the intelligent porous biodegradable polymer scaffold of the present invention has a highly interconnected pore structure where single pores having a size in the range of 100 to 300 μm are even distributed at both the outer surface and inside of the polymer scaffold, and there is no pore blockage at the outer surface. As a result of ESCA, EDAX and ELISA analyses, it has been found that ascorbic acid is introduced inside the dual pore structure of the intelligent porous biodegradable polymer scaffold, and BMP-2 is conjugated to the surface thereof.

Further, according to the same method as described in Example 1, the intelligent porous biodegradable polymer scaffold of the present invention was inoculated with muscle-derived stem cells, transplanted immediately into the damaged knee cartilage of a mouse, and then, cell differentiation was induced for 8 weeks. As a result, it has been found that the intelligent porous biodegradable polymer scaffold of the present invention can more efficiently induce in situ tissue regeneration of the musculoskeletal system in a living tissue than a polymer scaffold having no physiologically active substance (Comparative Example 1) or a polymer scaffold in which the physiologically active substance is introduced into only the surface thereof (Comparative Example 2).

Example 6

To a polymer solution in which a copolymer having a molecular weight of about 220,000 (glycolic acid:ε-caprolactone=65:35 w/w) is dissolved in chloroform at a concentration of 15% wt, an effervescent mixture (100 to 200 μm of particle size) of potassium carbonate and maleic acid (2:1 in molar ratio) was added so that the weight ratio of the effervescent mixture to the polymer solution was 95:5, followed by uniformly mixing with parathyroid hormone (PTH) at a concentration of 0.5% wt, to thereby obtain a polymer solution. The polymer solution was poured into a frame made of silicone, having a shape of a donut with a diameter of 8 mm, and followed by leaving it alone for 30 minutes to evaporate off the solvent, thereby obtaining a polymer sample having a disk shape. Then, the polymer sample was soaked in a mixed aqueous solution of water and ethanol (50:50 w/w) and subjected to foaming for 2 hours after undergoing ultrasonication for 30 seconds. After the foaming stage, the polymer sample was taken out and vacuum-dried at 40° C. for 2 hours to provide a biodegradable single pore polymer scaffold where PTH was introduced into the inside thereof.

The surface of the polymer scaffold obtained above was activated by treating with argon plasma, followed by graft-polymerization with acrylic acid, which modifies the hydrophilic surface of the polymer scaffold to be hydrophobic, due to the introduction of a carboxyl group into the surface thereof. Next, the polymer scaffold was soaked in a MES solution (pH 5.6) supplemented with 10 mg/ml of EDC (coupling agent) at 4° C. for 2 hours so that the carboxyl group of acrylic acid graft-polymerized onto the surface of the polymer scaffold was activated simultaneously while immobilizing heparin on the activated carboxyl group. The resulting polymer scaffold was taken out and soaked again in a PBS solution (pH 7.4) supplemented with RGD as a ligand peptide ($10^{-3}$ mole) at 37° C. for 1 hour, to thereby obtain an intelligent single pore biodegradable polymer scaffold where RGD is conjugated to the heparin fixed to the surface thereof.

The results of SEM analysis showed that the intelligent porous biodegradable polymer scaffold of the present invention has a highly interconnected pore structure where single pores having a size in the range of 100 to 200 μm are even distributed at both the outer surface and the inside of the polymer scaffold, and there is no pore blockage at the outer surface. As a result of ESCA, EDAX and ELISA analyses, it has been found that PTH is introduced inside the dual pore structure of the intelligent porous biodegradable polymer scaffold, and RGD is conjugated to the surface thereof. As a result of examining cell differentiation behavior by using bone marrow stem cells, it has been found that the intelligent porous biodegradable polymer scaffold of the present invention in which the physiologically active substances are introduced into both the surface and the inside thereof shows superior differentiation potential into chondrocytes over a polymer scaffold having no physiologically active substance (Comparative Example 1) and a polymer scaffold in which the physiologically active substance is introduced into only the surface thereof (Comparative Example 2).

Comparative Example 1

The porous biodegradable polymer scaffold having no physiologically active substance at both the surface and the inside thereof was prepared according to the same method as described in Example 1 except that dexamethasone and TGF-β1 as a physiologically active substance were not used.

Comparative Example 2

The porous biodegradable polymer scaffold in which TGF-β1 as a physiologically active substance is introduced into only the surface thereof was prepared according to the same method as described in Example 1 except that dexamethasone as a physiologically active substance were not used.

The porous biodegradable polymer scaffolds prepared in Comparative Examples 1 and 2 were subjected to in situ tissue regeneration experiment according to the same method as described in Example 1. As a result, in case of transplanting the polymer scaffold having no physiologically active substance according to Comparative Example 1, there was no differentiation from stem cells into chondrocytes, while in case of transplanting the polymer scaffold having the physiologically active substance only at the surface thereof according to Comparative Example 2, the partial differentiation from stem cells into chondrocytes was observed, but it was insignificant to induce in situ tissue regeneration.

While the present invention has been described and illustrated with respect to a number of embodiments of the invention, it will be apparent to those skilled in the art that variations and modifications are possible without deviating from the broad principles and teachings of the present invention, which is defined by the claims appended hereto.

What is claimed:

1. An intelligent porous biodegradable polymer scaffold for in situ tissue regeneration of the musculoskeletal system comprising:

a polymer scaffold having a surface modified with a carboxyl group-containing hydrophilic monomer;

a first physiologically active substance introduced into the inside of the polymer scaffold, wherein the first physiologically active substance is selected from the group consisting of dexamethasone, β-glycerophosphate, ascorbate-2-phosphate, ascorbate, demineralized bone matrix (DBM), hydroxyapatite (HAP), ascorbic acid, 1,25-dihydroxyvitamin $D_3$, tricalcium phosphate (TCP), collagen, parathyroid hormone (PTH), PTH 1-34 peptide, and retinoic acid-sensitive protein (CD-RAP); and a second physiologically active substance conjugated to the surface of the polymer scaffold via heparin immobilized on the hydrophilic monomer, wherein the second physiologically active substance is selected from the group consisting of dexamethasone, β-glycerophosphate, ascorbate-2-phosphate, ascorbate, demineralized bone matrix (DBM), hydroxyapatite (HAP), ascorbic acid, 1,25-dihydroxyvitamin $D_3$, tricalcium phosphate (TCP), collagen, parathyroid hormone (PTH), PTH 1-34 peptide, and retinoic acid-sensitive protein (CD-RAP).

2. The intelligent porous biodegradable polymer scaffold according to claim 1, wherein the polymer scaffold is made from a biodegradable polymer which is selected from the group consisting of polyglycolic acid (PGA), polylactic acid (PLA), polylactic acid-glycolic acid copolymer (PLGA), poly-ε-caprolactone (PCL), polyamino acid, polyanhydride, polyorthoester, derivatives, copolymers and mixtures thereof.

3. The intelligent porous biodegradable polymer scaffold according to claim 2, wherein the biodegradable polymer has a weight average molecular weight of 5,000 to 2,000,000.

4. The intelligent porous biodegradable polymer scaffold according to claim 1, wherein the carboxyl group-containing hydrophilic monomer is graft-polymerized onto the surface of the polymer scaffold in a molar ratio of 100:1 to 500:1.

5. The intelligent porous biodegradable polymer scaffold according to claim 1, wherein the first physiologically active substance is selected from the group consisting of dexamethasone, collagen, parathyroid hormone (PTH), PTH 1-34 peptide, and retinoic acid-sensitive protein (CD-RAP).

6. The intelligent porous biodegradable polymer scaffold according to claim 1, wherein the heparin is immobilized on the carboxyl group-containing hydrophilic monomer graft polymerized onto the surface of the polymer scaffold in a molar ratio of 100:1 to 500:1.

7. The intelligent porous biodegradable polymer scaffold according to claim 1, wherein the second physiologically active substance is selected from the group consisting of dexamethasone, collagen, parathyroid hormone (PTH), PTH 1-34 peptide, and retinoic acid-sensitive protein (CD-RAP).

8. The intelligent porous biodegradable polymer scaffold according to claim 1, wherein the second physiologically active substance is conjugated to the surface of the polymer scaffold in an amount of 0.01 to 50 n mol based on 1 g of the polymer scaffold.

9. The intelligent porous biodegradable polymer scaffold according to claim 1, wherein the first physiologically active substance is different from the second physiologically active substance.

10. The intelligent porous biodegradable polymer scaffold according to claim 1, which has a pore size in the range of about 10 to about 500 μm, a specific surface area per unit volume in the range of about 100 to about 500 cm$^3$/g, and a porosity in the range of about 90 to about 98%.

11. The intelligent porous biodegradable polymer scaffold according to claim 1, wherein the selected first and second physiologically active substances are different from each other.

12. The intelligent porous biodegradable polymer scaffold according to claim 1, wherein the selected first and second physiologically active substances are the same.

13. The intelligent porous biodegradable polymer scaffold according to claim 1, wherein the first and second physiologically active substances are independently selected from the group consisting of dexamethasone, β-glycerophosphate, ascorbate-2-phosphate, ascorbate, demineralized bone matrix (DBM), hydroxyapatite (HAP), ascorbic acid, 1,25-dihydroxyvitamin $D_3$, and tricalcium phosphate (TCP).

14. The intelligent porous biodegradable polymer scaffold according to claim 1, wherein the first and second physiologically active substances are independently selected from the group consisting of dexamethasone, β-glycerophosphate, ascorbate-2-phosphate, ascorbate, ascorbic acid, and 1,25-dihydroxyvitamin $D_3$.

15. The intelligent porous biodegradable polymer scaffold according to claim 1, wherein the first and second physiologically active substances are independently selected from the group consisting of dexamethasone, β-glycerophosphate, demineralized bone matrix (DBM), hydroxyapatite (HAP), tricalcium phosphate (TCP), collagen, parathyroid hormone (PTH), PTH 1-34 peptide, and retinoic acid-sensitive protein (CD-RAP).

16. The intelligent porous biodegradable polymer scaffold according to claim 1, wherein the first and second physiologically active substances are independently selected from the group consisting of dexamethasone, β-glycerophosphate, demineralized bone matrix (DBM), hydroxyapatite (HAP), and collagen.

17. The intelligent porous biodegradable polymer scaffold according to claim 1, wherein the first and second physiologically active substances are independently selected from the group consisting of dexamethasone and collagen.

18. The intelligent porous biodegradable polymer scaffold according to claim 1, wherein the first and second physiologically active substances are independently selected from the group consisting of dexamethasone, parathyroid hormone (PTH), and PTH 1-34 peptide.

19. The intelligent porous biodegradable polymer scaffold according to claim 1, wherein the first and second physiologically active substances are independently selected from the group consisting of dexamethasone and retinoic acid-sensitive protein (CD-RAP).

20. The intelligent porous biodegradable polymer scaffold according to claim 1, wherein the first and second physiologically active substances are independently selected from the group consisting of dexamethasone and demineralized bone matrix (DBM).

21. The intelligent porous biodegradable polymer scaffold according to claim 1, wherein the first and second physiologically active substances are both dexamethasone.

22. The intelligent porous biodegradable polymer scaffold according to claim 1, wherein the first and second physiologically active substances are both collagen.

23. The intelligent porous biodegradable polymer scaffold according to claim 1, wherein the first and second physiologically active substances are both retinoic acid-sensitive protein (CD-RAP).

24. The intelligent porous biodegradable polymer scaffold according to claim 1, wherein the carboxyl group-containing hydrophilic monomer is selected from the group consisting of acrylic acid methacrylic acid, maleic acid, itaconic acid, and aconitic acid.

25. An intelligent porous biodegradable polymer scaffold for in situ tissue regeneration of the musculoskeletal system comprising:
   a polymer scaffold having a surface modified with a carboxyl group-containing hydrophilic monomer;
   a first physiologically active substance introduced into the inside of the polymer scaffold, wherein the first physiologically active substance is dexamethasone; and
   a second physiologically active substance conjugated to the surface of the polymer scaffold via heparin immobilized on the hydrophilic monomer, wherein the second physiologically active substance is selected from the group consisting of dexamethasone, β-glycerophosphate, ascorbate-2-phosphate, ascorbate, demineralized bone matrix (DBM), hydroxyapatite (HAP), ascorbic acid, 1,25-dihydroxyvitamin $D_3$, tricalcium phosphate (TCP), collagen, parathyroid hormone (PTH), PTH 1-34 peptide, and retinoic acid-sensitive protein (CD-RAP).

26. The intelligent porous biodegradable polymer scaffold according to claim 25, wherein the polymer scaffold is made from a biodegradable polymer which is selected from the group consisting of polyglycolic acid (PGA), polylactic acid (PLA), polylactic acid-glycolic acid copolymer (PLGA), poly-ε-caprolactone (PCL), polyamino acid, polyanhydride, polyorthoester, derivatives, copolymers and mixtures thereof.

27. The intelligent porous biodegradable polymer scaffold according to claim 26, wherein the biodegradable polymer has a weight average molecular weight of 5,000 to 2,000,000.

28. The intelligent porous biodegradable polymer scaffold according to claim 25, wherein the carboxyl group-containing hydrophilic monomer is graft-polymerized onto the surface of the polymer scaffold in a molar ratio of 100:1 to 500:1.

29. The intelligent porous biodegradable polymer scaffold according to claim 25, wherein the carboxyl group-containing hydrophilic monomer is selected from the group consisting of acrylic acid, methacrylic acid, maleic acid, itaconic acid, and aconitic acid.

30. The intelligent porous biodegradable polymer scaffold according to claim 25, wherein the second physiologically active substance is selected from the group consisting of dexamethasone, β-glycerophosphate, ascorbate-2-phosphate, ascorbate, demineralized bone matrix (DBM), hydroxyapatite (HAP), ascorbic acid, 1,25-dihydroxyvitamin $D_3$, and tricalcium phosphate (TCP).

31. The intelligent porous biodegradable polymer scaffold according to claim 25, wherein the second physiologically active substance is selected from the group consisting of dexamethasone, β-glycerophosphate, ascorbate-2-phosphate, ascorbate, ascorbic acid, and 1,25-dihydroxyvitamin $D_3$.

32. The intelligent porous biodegradable polymer scaffold according to claim 25, wherein the second physiologically active substance is selected from the group consisting of dexamethasone, β-glycerophosphate, demineralized bone matrix (DBM), hydroxyapatite (HAP), tricalcium phosphate (TCP), collagen, parathyroid hormone (PTH), PTH 1-34 peptide, and retinoic acid-sensitive protein (CD-RAP).

33. The intelligent porous biodegradable polymer scaffold according to claim 25, wherein the second physiologically active substance is selected from the group consisting of dexamethasone, β-glycerophosphate, demineralized bone matrix (DBM), hydroxyapatite (HAP), and collagen.

34. The intelligent porous biodegradable polymer scaffold according to claim 25, wherein the second physiologically active substance is collagen.

35. The intelligent porous biodegradable polymer scaffold according to claim 25, wherein the second physiologically active substances is selected from the group consisting of dexamethasone, parathyroid hormone (PTH), and PTH 1-34 peptide.

36. The intelligent porous biodegradable polymer scaffold according to claim 25, wherein the second physiologically active substances is selected from the group consisting of dexamethasone and retinoic acid-sensitive protein (CD-RAP).

37. The intelligent porous biodegradable polymer scaffold according to claim 25, which has a pore size in the range of about 10 to about 500 μm, a specific surface area per unit volume in the range of about 100 to about 500 $cm^3/g$, and a porosity in the range of about 90 to about 98%.

* * * * *